United States Patent [19]

Kandler et al.

[11] Patent Number: 4,675,185
[45] Date of Patent: Jun. 23, 1987

[54] SOLUTION FOR STABILIZING RED BLOOD CELLS DURING STORAGE

[75] Inventors: Richard L. Kandler, McHenry; Gerald A. Grode, Grayslake, both of Ill.

[73] Assignee: Baxter Travenol Laboratories, Inc., Deerfield, Ill.

[21] Appl. No.: 806,062

[22] Filed: Dec. 6, 1985

[51] Int. Cl.$^4$ .................... A16K 35/14; A16K 35/18; A01N 1/02
[52] U.S. Cl. ........................................ 424/101; 435/2
[58] Field of Search ............................ 424/101; 435/2

[56] References Cited

U.S. PATENT DOCUMENTS 3,061,509 10/1962 Hart et al. .
3,393,206 7/1968 Cals et al. .
3,957,435 5/1976 Adams et al. .
4,181,609 1/1980 Wardlaw et al. .
4,267,269 5/1981 Grode et al. .
4,356,172 10/1982 Nakao et al. .
4,476,221 10/1984 Kane et al. .
4,572,899 2/1986 Walker et al. .
4,585,735 4/1986 Meryman et al. .

FOREIGN PATENT DOCUMENTS 1146769 5/1983 Canada .

OTHER PUBLICATIONS

National Technical Information Service Document—U.S. patent application No. 817,189, (Vora).
Bobyleva et al.—Chem. Abst., vol. 78 (1973), p. 93106n.

Primary Examiner—Sam Rosen
Attorney, Agent, or Firm—Paul C. Flattery; Bradford R. L. Price; Garrettson Ellis

[57] ABSTRACT

A solution for stabilizing red blood cells during storage contains, along with nutrients and other stabilizers, a safe and effective concentration of an inhibitor of a step of the glycolysis metabolic pathway which is subsequent to the step which forms 2,3-DPG. The inhibitor may be oxalic acid, sodium oxalate, potassium oxalate, or mixed salts thereof, for example.

10 Claims, No Drawings

SOLUTION FOR STABILIZING RED BLOOD CELLS DURING STORAGE

TECHNICAL FIELD

As described in Deindoerfer et al. U.S. Pat. No. 3,874,384, one problem which has arisen in the administration of blood stored for a period of days is that the red blood cells have a subnormal 2,3-DPG content. The result of this is that the stored red blood cells are less effective for several hours than would be desired in delivering oxygen to the tissues. In response to this, efforts of various kinds have gone forward to find ways to cause stored blood cells to retain higher levels of 2,3-DPG.

For example, in the article by G. W. Moore et al. entitled Improved Red Blood Cell Storage Using Optional Additive Systems (OAS) Containing Adenine, Glucose and Ascorbate-2-Phosphate, Transfusion (November-December, 1981) pp. 723–731, it is taught that sodium ascorbate-2-phosphate may be added to red blood cell storage solutions to improve 2,3-DPG levels in the stored red blood cells.

In the article by G. L. Moore et al. entitled Development of an Optimized Additive Solution Containing Ascorbate-2-Phosphate for the Preservation of Red Cells with Retention of 2,3 Diphosphoglycerate, Transfusion, Vol. 25, No. 4, (1985) pp. 319–324, an additive solution is disclosed which preserves 2,3-DPG concentrations in red blood cells. The solution contains adenine, ascorbate-2-phosphate, sodium phosphate, dextrose, and saline.

In the article by L. A. Wood et al. entitled The Effect of Ascorbate on the Maintenance of 2,3-Diphosphoglycerate (2,3-DPG) in Stored Red Cells, British Journal of Haematology, 1973, Vol. 25, pp. 611–618, ascorbic acid is added to red cell storage solution to prolong the maintenance of 2,3-DPG levels of stored blood.

In the co-pending patent application of Miripol et al. U.S. Ser. No. 748,513, filed June 25, 1985 entitled L-Ascorbate-2-Phosphate Salts in Blood Cell Storage, it is alleged that magnesium ascorbate-2-phosphate has significant advantages over sodium ascorbate-2-phosphate in red blood cell storage solutions.

Badwey and Westhead have noted that it has been shown that an inverse relationship exists between the activity of pyruvate kinase and the levels of 2,3-DPG. Badwey and Westhead, "Potential Regulation Properties of Human Erythrocyte Pyruvate Kinase", in *The Red Cell*, pp. 299–317, Alan R. Liss, Inc., New York, N.Y. 1978.

The invention of this application arose with the discovery that while certain samples of sodium and magnesium ascorbate phosphate were effective to maintain 2,3-DPG levels in stored red blood cells, an ultra-pure sample of magnesium ascorbate phosphate was relatively ineffective for that purpose. It is believed that ascorbate phosphate itself is not in fact responsible for increased 2,3-DPG maintenance in stored red cells. Accordingly, the conclusion was reached that an impurity present in the other samples was responsible for most of the maintenance of the 2,3-DPG levels in stored red blood cells. By further research, the active agent has been identified.

DESCRIPTION OF THE INVENTION

In this invention, a solution is provided for stabilizing red blood cells during storage. The solution may typically be based on a conventional red blood cell nutrient and storage solution, for example, ADSOL ® solution sold by Travenol Laboratories and described in Grode et al., U.S. Pat. No. 4,267,269. Alternatively, other red cell storage solutions may be used as well, or the inhibitor of this invention may be added to whole blood.

In accordance with this invention, one adds to a solution for stabilizing red blood cells during storage (such as the above solution) a safe and effective concentration of an inhibitor of the step of the glycolysis metabolic pathway which is subsequent to the step which forms 2,3-DPG. The glycolysis metabolic pathway for red blood cells is well known, being well described in biochemistry textbooks and the like. In this metabolic pathway, 2,3-DPG is first formed and then consumed. However, it has been found that if in a subsequent step of the metabolic pathway (which terminates with the creation of lactate), one of such subsequent steps are inhibited, the consumption of 2,3-DPG in the red blood cell is inhibited and the 2,3-DPG level of the red blood cells is maintained during storage. Thus they show more effective oxygen transport immediately after infusion.

For example, it is possible to inhibit the enzyme lactate dehydrogenase (LDH) which catalyzes the pyruvate to lactate step of the glycolysis metabolic pathway. This, in turn, causes the process to apparently "back up", with consequent inhibition of the step in the pathway which consumes 2,3-DPG.

Speciific inhibitors which may be used include the oxalate group or a phosphooxalate derivative thereof. Specifically, oxalic acid may be used or an alkali metal oxalate, generally sodium or potassium oxalate, or mixed or acid salts thereof. Additionally, a phosphorylated derivative of oxalate may also be used, for example, sodium or potassium phosphooxalate, or mixed or acid salts thereof. One structural formula for a phosphooxalate radical may be as follows, the sodium salt being specifically shown:

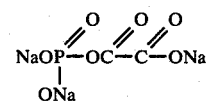

Likewise, the oxamate group is a known LDH inhibitor and may be used as an equivalent to oxalate, as the free acid, sodium or potassium salts, or mixtures thereof.

Typically, the inhibitor may be present in a concentration of at least 2 mg. per liter of stabilizing solution, but less than a concentration that permits precipitation of calcium oxalate or phosphooxalate on infusion of the red blood cell storage solution to a patient. The oxalate ion can precipitate in the form of calcium oxalate when infused or ingested by a human being, with toxic results. However, the oxalate ion is not notably toxic if it is provided in a low concentration that prevents precipitation of calcium oxalate (or phosphooxalate) upon infusion of the solution to the patient. Such a limiting concentration is generally dependent on the amount of solution infused.

Typically, from 0.2 to 20 mg. of the inhibitor of this invention may be present per 100 ml. of red blood cell stabilizing solution, and most preferably about 0.5 to 10 mg. per 100 ml. of solution.

Typically it is desired for the inhibitor of this invention to be present in a minimum concentration capable of providing the desired effect. One reason for this is that ATP levels in red blood cells can drop in a manner which is dependent upon the concentration of the inhibitor of this invention.

Specifically, a red cell storage solution made in accordance with this invention may contain, per 100 ml. of solution, 2000 mg. of dextrose anhydrous, 900 mg. sodium chloride, 750 mg. mannitol, 27 mg. adenine, and 0.5 to 10 mg. of oxalic acid or sodium oxalate, the balance of the solution being sterile, pyrogen-free water. 100 ml. of the above solution may be placed into a suitable container such as a Fenwal blood bag (manufactured by Travenol Laboratories, Inc., Deerfield, Ill.) and sealed therein. The bag may then be sterilized by autoclaving, for example.

The bag may be a satellite bag of a multiple Fenwal blood bag, interconnected by tubing for sterile connection between the respective bags. Blood is collected into one of the bags which do not contain the cell storage solution of this invention. The bag system and blood are then centrifuged; the plasma portion expressed from the collection bag into a different bag. The storage solution of this invention then may be expressed into the bag containing the remaining packed red cells, or the packed red cells may be expressed into the bag containing the storage solution. The bag containing the packed red cells and storage solution of this invention may then be separated and stored at 4° C. for a period of days until the cells are needed. Upon assay several days later, it will be found that the 2,3-DPG level of the stored red cells is significantly higher than red cells which have been stored in an identical solution without oxalate.

More generally, a preferred cell storage solution may be that as described in the previously cited Grode et al. patent, in which the cell storage solution contains, per 100 ml. of solution, essentially from 5 to 50 mg. of adenine, from 1000 to 3500 mg. of dextrose or fructose, from 400 to 1200 mg. of sodium chloride, and from 250 to 200 mg. of mannitol, and containing an inhibitor of this invention in safe and effective quantity, essentially all of the balance of the solution being sterile, pyrogen-free water.

The above subject matter, and the examples below, are provided for illustrative purposes only, and are not intended to limit the scope of the invention of this application, which is as defined in the claims below.

EXAMPLE I

One unit of fresh packed red cells, collected into Citrate Phosphate Dextrose solution, was aliquoted into 10 ml. portions in test tubes. To each of these portions was added 4.5 ml. of a test additive solution. The tubes of cells were then allowed to stand for 22 hours at room temperature. The results are illustrated in Table I below. Each individual experiment was repeated several times, and the measurements of 2,3-DPG indicate the range of concentrations of 2,3-DPG in the various groups of identical samples.

TABLE I

| Test Additive Solution | Concentration of 2,3-DPG in red cells at beginning of experiment ($\mu$mol./ml.) | Concentration of 2,3-DPG in red cells 22 hours later ($\mu$mol./ml.) |
| --- | --- | --- |
| A. Red cell storage solution having, per 100 ml., 2000 mg. dextrose, 900 mg. sodium chloride, 750 mg. mannitol, 27 mg. adenine, balance water (pH 5.2–6–8). | 1.65–2.52 (six samples) | 0.08–0.30 |
| B. 1 millimolar oxalic acid solution | 1.92–1.97 (three samples) | 2.00–2.33 |
| C. 10 millimolar oxalic acid solution | 1.45–2.12 (three samples) | 1.94–2.12 |
| D. 1 millimolar potassium oxalate solution | 2.07–2.28 (three samples) | 2.90–2.93 |
| E. 0.1 millimolar potassium oxalate solution | 2.15–2.19 (three samples) | 1.63–1.79 |
| F. 0.5 millimolar potassium oxalate solution | 2.17 (three samples) | 2.28–2.52 |

It can be seen from Section A of Table I that when a commercial red cell storage solution is added to the red cells, no good protection is imparted against a rapid reduction of 2,3-DPG in the red cells. After 22 hours of storage, only a tiny percentage of the original 2,3-DPG concentration remains.

However, when oxalate is present as in Sections B–F of Table I, very significant maintenance of 2,3-DPG levels are noted over a 22 hour period.

EXAMPLE II

The experiment of Example I was repeated, except that instead of making use of test tubes for storage of the red blood cells, packed cell units in storage Fenwal blood bags were stored in conjunction with 100 ml. of the test solution as shown below and stored for 14 days at 4° C. The test results are as shown in Table II below:

TABLE II

| Test Additive Solution | Concentration of 2,3-DPG in red cells at beginning of experiment ($\mu$mol/gram of hemoglobin) | Concentration of 2,3-DPG in red cells 14 days later ($\mu$mol/gram of hemoglobin) |
| --- | --- | --- |
| A. The solution of Table 1A | 9.69–11.89 (two samples) | 0.33–0.89 |
| B. The solution of Table 1A containing a concentration of 1 millimolar potassium oxalate | 10.0–10.8 (two samples) | 15.02–15.66 |
| C. The solution of Table 1A containing a concentration of 10 millimolar potassium oxalate | 9.38–11.26 (two samples) | 14.49–15.92 |
| D. The solution of Table 2C containing purified magnesium ascorbate-phosphate at 16 millimolar | 11.69–14.99 (two samples) | 15.66–17.66 |

TABLE II-continued

| Test Additive Solution | Concentration of 2,3-DPG in red cells at beginning of experiment (μmol/gram of hemoglobin) | Concentration of 2,3-DPG in red cells 14 days later (μmol/gram of hemoglobin) |
|---|---|---|
| concentration. | | |

That which is claimed is:

1. The method of maintaining 2,3-DPG concentration in human red blood cells during storage which comprises placing said red blood cells into a red blood cell nutrient and storage solution which includes from 0.2 to 20 mg. per 100 ml. of said solution of an inhibitor consisting essentially of oxalic acid, an alkali metal oxalate, or phosphooxalate salts thereof, and storing said red blood cells for a period of days in said solution under reduced temperature conditions.

2. The solution of claim 1 which also includes, per 100 ml. of solution, essentially from 5 to 50 mg. of adenine, from 1000 to 3500 mg. of dextrose or fructose, from 400 to 1200 mg. of sodium chloride, and from 250 to 2000 mg. of mannitol.

3. The method of claim 1 in which from 3 to 20 mg. of said inhibitor is present per 100 ml. of said solution.

4. The method of claim 1 in which said red blood cells are administered to the blood stream of a patient after storage.

5. The method of claim 1 in which from 0.5 to 10 mg. of said inhibitor is present per 100 ml. of said solution.

6. The method of maintaining 2,3-DPG concentration in human red blood cells which comprises, placing said cells in a red cell nutrient and stabilizing solution, said nutrient and stabilizing solution including from 0.2 to 20 mg. per 100 ml. of said solution of an inhibitor of the glycolysis metabolic pathway which is subsequent to the step which forms 2,3-DPG, said solution also including, per 100 ml. of solution, essentially from 5 to 50 mg. of adenine, from 1000 to 3500 mg. of dextrose or fructose, from 400 to 1200 mg. of sodium chloride, and from 250 to 2000 mg. of mannitol, and storing said solution containing red blood cells for a period of days in a reduced temperature environment.

7. The method of claim 6 in which said inhibitor consists essentially of oxalic acid, an alkali metal oxalate, or phosphooxalate salts thereof.

8. The solution of claim 6 in which from 3 to 20 mg. of said inhibitor is present per 100 ml. of said solution.

9. The method of claim 6 in which said red blood cells are administered to the blood stream of a patient after storage.

10. The method of claim 6 in which from 0.5 to 10 mg. of said inhibitor is present per 100 ml. of said solution.

* * * * *